US006383152B1

(12) United States Patent
Hartmann et al.

(10) Patent No.: US 6,383,152 B1
(45) Date of Patent: May 7, 2002

(54) APPARATUS FOR PRODUCING SHOCK WAVES FOR TECHNICAL, PREFERABLY MEDICAL APPLICATIONS

(75) Inventors: Werner Hartmann, Grossenseebach; Joerg Kieser, Forchheim, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/360,945

(22) Filed: Jul. 26, 1999

Related U.S. Application Data

(63) Continuation of application No. PCT/DE98/00184, filed on Jan. 21, 1998.

(30) Foreign Application Priority Data

Jan. 24, 1997 (DE) ........................................ 197 02 593

(51) Int. Cl.[7] ................................................ A61B 17/22

(52) U.S. Cl. ............................................ 601/4; 367/163

(58) Field of Search ......................... 601/2, 4; 367/146, 367/147, 163, 166, 174

(56) References Cited

U.S. PATENT DOCUMENTS 3,680,397 A * 8/1972 Haeusler et al. ............... 72/56
4,697,588 A * 10/1987 Reichenberger ................ 601/4
4,796,608 A * 1/1989 Koehler
4,840,166 A * 6/1989 Naser et al.
5,056,069 A * 10/1991 Granz et al.
5,233,972 A * 8/1993 Rattner et al. ................. 601/4
5,251,614 A * 10/1993 Cathignol et al.
5,309,897 A * 5/1994 Hassler et al. ................. 601/4
5,317,229 A * 5/1994 Koehler et al. ............. 310/334
6,113,560 A * 9/2000 Simnacher

* cited by examiner

*Primary Examiner*—Marvin M. Lateef
*Assistant Examiner*—Shawna J. Shaw
(74) *Attorney, Agent, or Firm*—Herbert L. Lerner; Laurence A. Greenberg; Werner H. Stemer

(57) ABSTRACT

An apparatus produces intense pressure waves as shock waves for technical and preferably medical applications, especially for lithotripsy and/or pain therapy. Acoustic waves of high energy density are produced through the use of pressure pulsations. The pressure waves are produced by briefly heating a conductive electrolyte, whereby electric energy is converted directly and very largely without losses with the aid of an electric pulse for the purpose of heating up the electrolyte. The apparatus includes two electrodes which enclose the electrolyte and are controlled by a power pulse generator for outputting sound waves into a sound propagation medium.

30 Claims, 3 Drawing Sheets

APPARATUS FOR PRODUCING SHOCK WAVES FOR TECHNICAL, PREFERABLY MEDICAL APPLICATIONS

CROSS-REFERENCE TO RELATED APPLICATION

This application is a continuation of copending International Application No. PCT/DE98/00184, filed Jan. 21, 1998, which designated the United States.

BACKGROUND OF THE INVENTION

FIELD OF THE INVENTION

The invention relates to an apparatus for producing shock waves for technical, preferably medical, applications, in particular for lithotripsy or pain therapy, in which mechanical waves with high energy density are produced through the use of pressure pulsations.

Intense sound waves or shock waves with working pressures in a range of several $10^7$ Pa up to $10^8$ Pa are used for various applications. One example is lithotripsy in medicine, in which focused pressure waves generated outside the body are used to generate a strong shock wave at the location of gallstones or kidney stones, which is so strong that the stone disintegrates into small fragments which can leave the body in the natural way without surgical intervention. Typically, several hundred to several thousand shock wave applications, i.e. individual pulses, are required to ensure sufficiently high fragmentation of the stone.

In order to generate the latter shock waves, there is a need for a shock wave generator which generates a sound wave that is already focused or can be focused by lenses, in particular acoustic lenses, and the focus of which must be at the location of the stone to be destroyed. The focal length of the acoustic configuration should be small, i.e. in the range of some tens of centimeters, in order to limit the energy density at the surface of the patient's body, i.e. to <1 J/cm$^2$. That permits the pain caused by the passage of the sound to be controlled by local anesthetics.

The pulse repetition rate should be about 1 to 5 per second for an acceptable treatment time. The life of the shock wave generator should be as long as possible, i.e. several million pulses, to allow a relatively large number of patients to be treated without the need for servicing or repair work. The properties of the shock wave generator, in particular shock wave energy, pulse duration, position of the focus etc., should only change slightly, if at all, during its entire life in order to permit constant, reproducible results. The shock waves should be generated in water or in liquids with acoustic properties comparable to those of water to ensure efficient propagation and transmission of the sound into the body of the patient through a suitable acoustic impedance between the shock wave generator and the body. The focus diameter of the focused shock wave at the location of the stone (~cm) should be comparable with the diameter of the stone to ensure an efficient interaction between the shock wave and the stone. Typical wavelengths for the shock wave are in a range from 1 to 10 mm, corresponding to pulse durations of, typically, ~1 $\mu$s. Quality requirements at the wave front in the shock wave generator to enable the required focusing ability to be achieved are correspondingly high.

The requirements are similar in other technical applications, e.g. in recycling through the use of shock waves, in cleaning surfaces through the use of shock waves, in mining, breaking up rock without the use of chemical explosives, for example, in geology and in oceanography, for sonar applications for example. In some of those applications, considerably higher and, in some cases, more variable, pulse energies are required than in lithotripsy. Therefore, a virtually arbitrarily scaleable shock wave generator principle would be very useful for many applications.

Apart from using chemical explosives, the following three principles are the only ones used heretofore for generating shock waves. According to those principles, electrical energy is converted to acoustic energy in the form of intense shock waves:

- the electrohydraulic principle involving the generation of a spherically expanding pressure wave through the use of an underwater spark and, if required, focusing with ellipsoidal reflectors, such as is described in Rev.Sc. Instrument 65 (1994), pp. 2356–2363 and Biomed. Tech. 22 (1977), p. 164 ff;
- the piezoelectric principle involving the generation of a pressure wave by using pulsed piezoelectric sound transducers, as described, for example, in German Published, Non-Prosecuted Patent Application DE 33 19 871 A1, corresponding to U.S. Pat. No. 4,858,597; and
- the electromagnetic principle involving the generation of a pressure wave through the use of an electromagnetically driven diaphragm, which is described in detail in Appl. Phys. Lett. 64 (1994), pp. 2596–2598 and Acustica 14 (1964), p. 187.

Particularly in the case of the principle first mentioned above, the main disadvantages are short service life, poor reproducibility and limited scaleability of the shock wave transducers, and short service life, e.g. just a few thousand pulses due to electrode erosion and an associated fluctuation in the position of the focus, which in particular present problems. Piezoelectric transducers likewise have a very limited mechanical service life at the amplitudes which are required in that case. At present, electromagnetic sound transducers have the longest service lives, typically ~1 million pulses. However, for reasons connected with their ability to withstand electrical and mechanical loading, they can only be scaled to a limited extent. Extending the service life to several million pulses would be advantageous, as would wider scaleability of the shock wave energy and pulse shape.

In order to implement the electrohydraulic principle, German Patent DE 0 911 222 C has disclosed a sound transmitter in which the sound pressure is generated when a current passes through shock-like vaporizations brought about in narrowly defined liquid filaments. German Published, Prosecuted Patent Application DE 10 76 413 B has already disclosed a sound generating method in which a field line contraction on a wire or at an end of a wire or at the constriction caused by a flexible insulating body is used to achieve a high field density and consequently a high power density in the immediate vicinity of the wire. However, that only allows small volumes in the immediate vicinity of the wire or at the constriction to be used. As a result, on one hand the majority of the energy is converted at low energy density in large volumes, thereby drastically reducing the energy content of the pressure wave and efficiency and, on the other hand the achievable energy is very small due to the small volume. In practice, connecting a large number of such channels in parallel has the effect that, due to slight differences between the channels, a single channel is preferred and it is then heated up to a greater extent than the others. The earlier and higher current flow resulting from the higher temperature generally leads to a flashover of high current intensity and, because of the non-linearity of the processes leading to the flashover, the principle can thus only be used at safe power densities well below the breakdown strength of the electrolyte. That imposes a severe limit both on the amplitude and on the efficiency of such a pulsed sound source. Even slight differences in the channels lead to significant fluctuations in the associated pressure amplitudes. As a result, homogeneous wave fronts can only be produced to a limited extent with such a system.

Finally, U.S. Pat. No. 5,105,801 has disclosed a configuration in which two discharge electrodes are aligned with an internal focus within an electrolyte volume disposed in a parabolic reflector, thus producing sound waves which can be focused on points outside the reflector.

SUMMARY OF THE INVENTION

It is accordingly an object of the invention to provide an apparatus for producing shock waves for technical, preferably medical applications, which overcomes the hereinafore-mentioned disadvantages of the heretofore-known devices of this general type, which operates by a thermohydraulic method and through the use of which several million pulses can be generated without problems of wear.

With the foregoing and other objects in view there is provided, in accordance with the invention, an apparatus for producing shock waves for technical, preferably medical, applications, in particular for lithotripsy or pain therapy, comprising a conductive liquid electrolyte; two electrodes enclosing the conductive liquid electrolyte; and a power pulse generator controlling the electrodes with an intense electric pulse for converting electrical energy directly and very largely without losses to briefly heat the conductive liquid electrolyte and produce pressure pulsations output as acoustic sound waves of specified wavelength and high energy density into a sound propagation medium.

The invention starts from the fact that a highly conductive electrolyte is heated up briefly through the use of an intense electric pulse and the electric energy being input is converted directly and very largely without losses into thermal energy of the electrolyte. The heat can be applied simultaneously and homogeneously to relatively large, scaleable volumes and large, likewise scaleable surfaces. When heating up a large-area layer of liquid by direct current flow, the current density and electric field strength within the layer of liquid remain largely constant, with the thickness of the layer of liquid being less than the wavelength to be produced but the transverse dimension being large in comparison. In a suitable medium, the thermal expansion of the heated electrolyte produces a rise in pressure and therefore, given suitable boundary conditions, it produces a pressure wave which can propagate in this medium.

Almost any desired scaleability and geometry in combination with virtually wear-free performance of such a thermohydraulic shock wave transducer is possible due to the principle according to the invention. In contrast to the electrohydraulic principle, there is generally no concentration in the current flow due to plasma formation at individual points on the electrodes. Therefore, the operation of such a configuration does not lead to erosion of the electrodes, thereby making it possible to achieve a long service life. Due to the spatially homogeneous power loading of the electrolyte, the membrane or acoustically "permeable" electrode is subject to very homogeneous mechanical loading, thereby likewise greatly increasing the service life of the membrane in comparison with electromagnetic sound transducers.

Overall, configurations in accordance with the present invention have the advantage of permitting large volumes to be subjected to uniform and homogeneous loads over a large area up to the limit of breakdown strength. This is due to the deliberate avoidance of structures which intensify the field, such as wires, peaks, edges or constrictions in the current-bearing area. Thus there is no limitation with regard to pulse energy and scaleability. The advantage of the new configuration is, in particular, that the wave fronts which arise are very uniform, with the result that a pulsed sound source that can be scaled in a virtually unlimited manner is provided and in addition a high-quality wave front is obtained.

Other features which are considered as characteristic for the invention are set forth in the appended claims.

Although the invention is illustrated and described herein as embodied in an apparatus for producing shock waves for technical, preferably medical applications, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
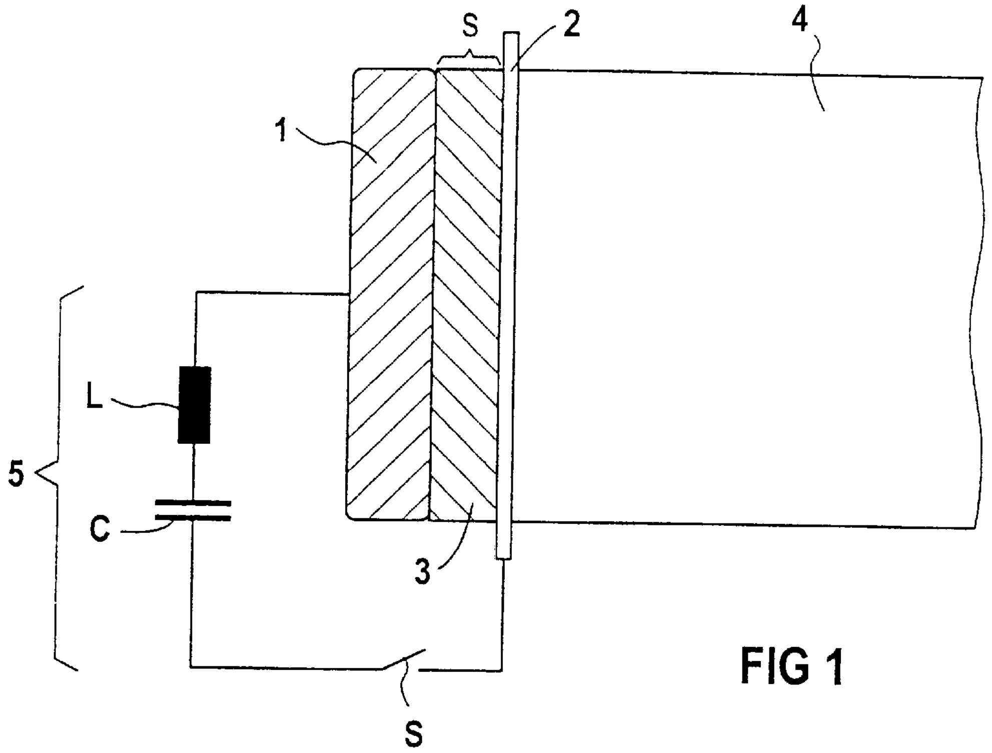
FIG. 1 is a fragmentary, diagrammatic and schematic view of a thermohydraulic shock wave generator with flat electrodes and an associated power pulse generator.

Referring now to the figures of the drawings in detail and first, particularly, to FIG. 1 thereof, there is seen an illustration of the principle underlying a thermohydraulic sound transducer with flat electrodes. In accordance with the geometry of the configuration, such an embodiment produces a flat sound wave, which can be focused by an acoustic lens that is disposed, if required, on an output side. The sound transducer includes a solid fixed electrode 1, a thin and lightweight electrode 2 at a distance s from the electrode 1 and media in the form of an electrolyte 3 having a layer thickness s and a sound propagation medium 4.

The fixed electrode 1 and the diaphragm-shaped electrode 2 are both manufactured from materials that are resistant to corrosion by the media 3 and 4 and have smooth surfaces to prevent the formation of localized discharges due to excessive field strength at peaks, etc.

A product of density and sound velocity of the electrode 1 is significantly larger than products of these quantities in the electrolyte 3 and the sound propagation medium 4. As far as possible, an acoustic impedance of the electrolyte 3 and the sound propagation medium 4 should be equal and correspond approximately to that of water, i.e. the main component of the human body. This is done to ensure good acoustic matching between the sound transducer and the body of the patient. It is expedient if gas-free fully demineralized water is used as the sound propagation medium 4 and a conductive salt solution is used as the electrolyte 3.

A particularly simple embodiment uses the same material for the sound propagation medium 4 as for the electrolyte 3.

Liquids other than water but with comparable electrical and acoustic properties can also be used for this purpose. Particularly for applications other than in lithotripters, it is worthwhile to match the acoustic impedance of the media 3 and 4 to that of the coupling medium. This is particularly important for applications other than medicine, such as for breaking up rock through the use of shock waves, for example.

A power supply to the electrode 2 must have a symmetrical layout to ensure a desired symmetry in a pressure wave to be produced by symmetrical distribution of current and power in the electrolyte 3. For this purpose, it is advantageous to maintain a coaxial power supply to the electrodes 1 and 2.

A power pulse generator 5 which is connected to the electrodes 1 and 2 supplies electrical energy in the form of short pulses with a duration of, typically, $\mu$s. In the simplest case, the pulse generator includes an energy storage device or accumulator in the form of a high-voltage capacitor C, a quick-closing switching element S and an inductance L formed from the supply lines. When the switch S is closed, the capacitor C is discharged through the inductance L and the switch S into the electrolyte which has an internal resistance R. An energy content E of the storage device or accumulator is:

$$E=C*U^2/2$$

where U is the charging voltage of the capacitor. This heats the electrolyte by a temperature difference:

$$\Delta T=E/(\rho_m*C_h*A*s),$$

where ρm is the density of the electrolyte (~1.0 g/cm$^3$ for aqueous solutions), $C_h$ is the heat capacity of the electrolyte and A*s is the volume of the electrolyte (=area A*thickness s). Given sufficiently short pulses in the $\mu$s range, heat conduction is negligible. This results in electrolyte expansion by:

$$\Delta V/V=\alpha*\Delta T$$

where α is the expansion coefficient. Where $$r>>s$$

and $$s<\lambda,\ r>\lambda$$

with 2*r=diameter of electrodes 1 and 2, λ=length of a shock wave, $\lambda=c_s*\tau$ where $c_s$=sound velocity in the media 3 and 4 and τ=pulse duration, the electrolyte expands almost exclusively in a direction perpendicular to the electrode surface. The following is obtained:

$$\Delta s/s\sim\Delta V/V=\alpha*\Delta T$$

for the relative change in layer thickness. This change in s is reduced by the finite sound velocity $c_s$ over a distance $$\lambda'=s+\lambda$$

due to the finite compressibility k of the media 3 and 4. If k and $c_s$ are assumed to be identical for both media 3 and 4, the following is obtained for the mean pressure rise within the range λ':

$$\Delta p=\alpha*E/[(s+\lambda)*\kappa*\rho_m*C_h*A]$$

and, where s <<λ, i.e. where the layer thickness s is negligible in comparison with the width of the shock wave λ:

$$\Delta p=\alpha*E/[c_s*\tau*\kappa*\rho_m*C_h*A]$$

This means that the amplitude of the pressure rise is independent of the layer thickness s.

When using an aqueous solution or ethanol for the media 3 and 4, the values of α, $c_s$, κ, ρ, and $C_h$ can be taken from the literature. The following values are obtained:

| Symbol | Parameter | Water | Ethanol | Unit |
|---|---|---|---|---|
| $\alpha$ | Expansion Coefficient | $2.07*10^{-4}$ | $11*10^{-4}$ | 1/K |
| $c_s$ | Sound Velocity | 1480 | 1170 | m/s |
| $\kappa$ | Compressibility | $0.5*10^{-9}$ | $1.17*10^{-9}$ | 1/Pa |
| $\rho_m$ | Density | $10^3$ | 789 | kg/m$^3$ |
| $C_h$ | Heat Capacity | $4.18*10^3$ | $2.43*10^3$ | J/kg |

Given a pulse energy of 200 J, an electrode surface area A=100 cm$^2$=10$^{-2}$ m$^2$ and a pulse duration of τ~5 $\mu$s, a flat pressure wave with a mean amplitude of:

$$\Delta p\sim 2.66*10^5 N/m^2\sim 2.6\ bar$$

is obtained in aqueous electrolytes and a mean amplitude of:

$$\Delta p\sim 1.6*10^6 N/M^2\sim 16\ bar$$

is obtained in an electrolyte having a main constituent which is ethanol.

This pressure rise propagates through the medium 4 as a flat wave perpendicular to the surface of the electrode 1 and can be focused by an acoustic lens. Typical focus diameters $2*r_f$ of:

$$2*r_f\sim\lambda$$

are achieved, i.e. the flat wave is compressed by one to two orders of magnitude, which leads to a corresponding pressure increase at the focus.

The peak pressures that can be achieved at the focus can be scaled within a wide range by increasing A. With the aid of the configuration described, it is thus possible to generate shock waves with amplitudes in a range >100 bar that are suitable for use in lithotripters and it is possible to do this in a reproducible manner and virtually without wear.

An increase in the pressure can be obtained by shortening the pulse duration, since the energy deposited in the electrolyte is distributed over a small volume and the pressure rise is accordingly dissipated over a shorter distance, because of the finite sound velocity. With the same pulse energy of 200 J and a pulse duration of just τ=1 $\mu$s, the initial pressure is already Δp~10 bar when using an aqueous electrolyte.

An additional increase in pressure can be achieved by the use of specific electrolytes as the medium 3: liquids with a low heat capacity and low compressibility in combination with a high thermal expansion coefficient are particularly advantageous. One example is ethanol mixed with ion-conducting additives. A suitable additive for achieving the required conductivity is a portion of water containing a dissolved salt. In the example quoted above (E=200 J; τ=1 $\mu$s) pressures on the order of Δp~40 bar are obtained when using ethanol. The use of polyhydric alcohols that are not inflammable at room temperature, such as ethylene glycol or glycerol containing salts soluble therein, e.g. magnesium perchlorate or lithium chloride, is particularly advantageous.

Figure 2:
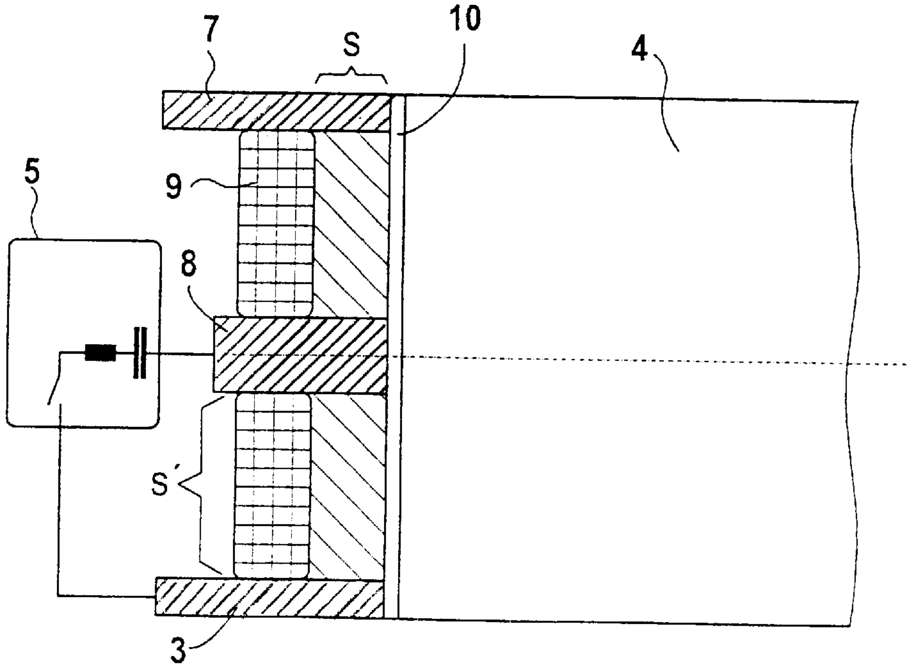
FIG. 2 is a view similar to FIG., 1 of a rotationally symmetrical thermohydraulic shock wave generator and an associated power pulse generator with a radial electrode configuration and radial current flow.

As is shown in FIG. 2, an advantageous embodiment employs an electrode configuration with current flow in the radial direction instead of the axial direction and thus allows higher operating voltages at the electrolyte 3. The power pulse is applied to an electrode 8 which is concentric about an axis of symmetry and to a cylindrical or annular electrode 7 disposed coaxially to the electrode 8. In this embodiment, in which rotational symmetry is assumed, the current flows in the radial direction between the electrodes 7 and 8 in the electrolyte 3. This means that, in this case the current flows perpendicular to the direction of sound propagation, in contrast to FIG. 1 where a current flows in the liquid layer in the preferential direction of sound propagation. The electrolyte 3 having the layer thickness s is delimited from the propagation medium 4 by an insulating plate 9 on one side and by a likewise insulating diaphragm 10 on the other side, in order to limit current flow to the volume having the electrolyte thickness s. An electrode flashover distance s' is thereby increased from the distance s to approximately the radius of the configuration. This allows significantly higher voltages at the electrodes without the risk of a breakdown in the electrolyte. This makes it possible to produce a significantly higher energy density in the electrolyte 3, leading to considerably higher pressure amplitudes than in the case of axial current flow.

Figure 3:
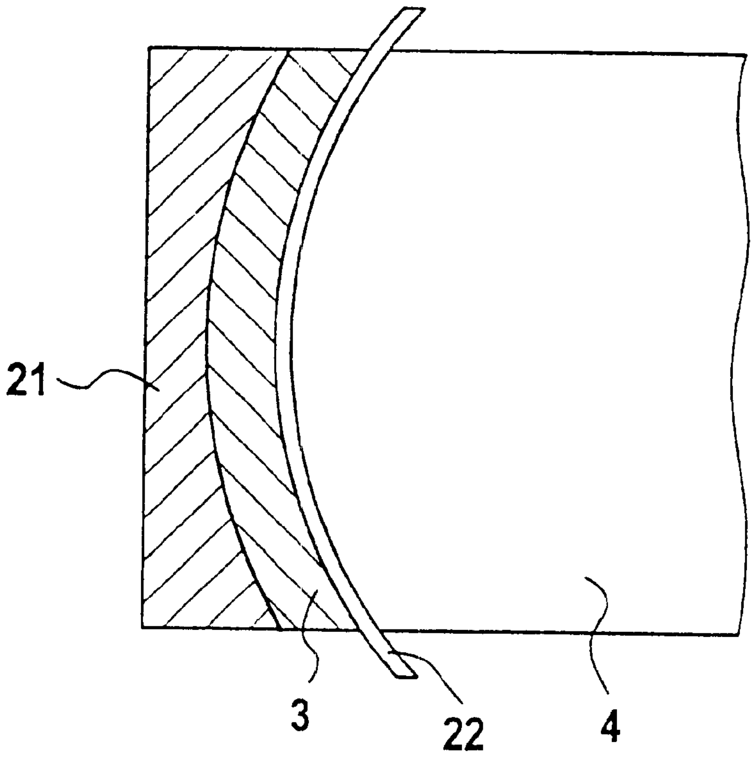
FIG. 3 is a fragmentary, sectional view of a thermohydraulic shock wave generator with concave electrodes.

As is shown in FIG. 3, focusing of the pressure wave is advantageously achieved by the fact that two electrodes 21 and 22 have a concave construction rather than a flat construction. This gives rise to a curved wave front which leads to a concentrically converging pressure wave which has a pronounced focus at a focal point of the reflector formed by the surface of the electrode 21. In this self-focusing configuration, it is possible to dispense with an acoustic lens, thus eliminating image distortion and losses associated with the lens.

Constructing the electrodes 21 and 22 in convex form would lead to the formation of spherically expanding shock waves, which can be used, for example, for ultrasonic tomography in medicine and in general engineering for sonar systems in water and in the earth's crust, so-called "geo-mapping".

In further non-illustrated advantageous embodiments, the electrodes 1 and 2 can have a geometry other than a flat or spherical geometry. When using cylindrical electrode shapes, it is possible, for example, to produce a line focus, which can be used to advantage for the precise cutting of brittle objects such as semiconductor wafers, glass workpieces, ceramic substrates, optical components, ceramic tiles, etc. or for cleaning relatively large castings. Adapting the geometry and electrical parameters makes it possible to optimize a thermohydraulic shock wave generator for virtually any application in which high mechanical forces are only briefly required, i.e. in shock form.

It is possible to place a regular or irregular grid structure between the two electrodes 1 and 2. This serves to define the distance between the two electrodes and thus prevents the distance which is necessary to avoid flashovers from falling below a minimum. An insulating plastic with a dielectric constant similar to that of the electrolyte 3 used between the electrodes 1 and 2 is expediently used as the material for the grid. This prevents the occurrence of local excesses in field strength at triple points of the transition of the electrode-grid-medium 3, which could otherwise lead to unwanted flashovers.

The coupling with the pulse generator is decisive for the dimensioning of the shock wave generator. Given an impedance Z of $Z=\sqrt{L/C}\sim 1\ \Omega$ that is typical for power pulse engineering, an internal resistance of R~1 Ω is required for the electrolyte. The internal resistance R of the electrolyte is calculated from $R=\rho*s/A$, which gives a resistivity ρ of $\rho=A*R/s=10^3\ \Omega*\text{cm}$.

A corresponding resistivity is achieved, for example, through the use of aqueous salt solutions with concentrations in a range C~1 g/l if the surface area A is dimensioned in a range A~100 $cm^2$ and the electrode spacing s is dimensioned as s≅1 mm.

A dielectric strength $U_{max}$ in water of $U_{max}$~10 kV is achieved at an electrode spacing of s=1 mm. This corresponds to the maximum peak voltage applied briefly to the electrolyte at a charging voltage of 20 kV. The dimensioning of the shock wave generator and the power pulse generator thus corresponds to the prior art used in similar equipment and do not impose difficult conditions on the components.

In specific embodiments, it is possible to dispense both with concave shaping of the electrodes and with a refractive acoustic lens in the "thermohydraulic shock wave generator" described. This can be achieved by structuring the surface of an acoustically reflecting ("hard") electrode in such a way that a plane or concave focusing surface is maintained within permissible tolerances at the center but that focusing of annular components of the reflected flat sound wave at a common focus is performed by radially symmetric structures. The structures must have such small dimensions in the radial direction that unavoidable deviations from the intended common focus position can be tolerated and the electric resistance between the two electrodes is not impaired by likewise unavoidable differences in height of the surface structures as well.

Figure 5:
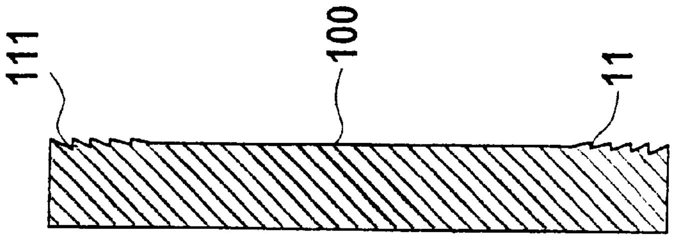
FIGS. 4 and 5 are respective plan and sectional views of a specific embodiment of a focusing electrode.
Figure 4:
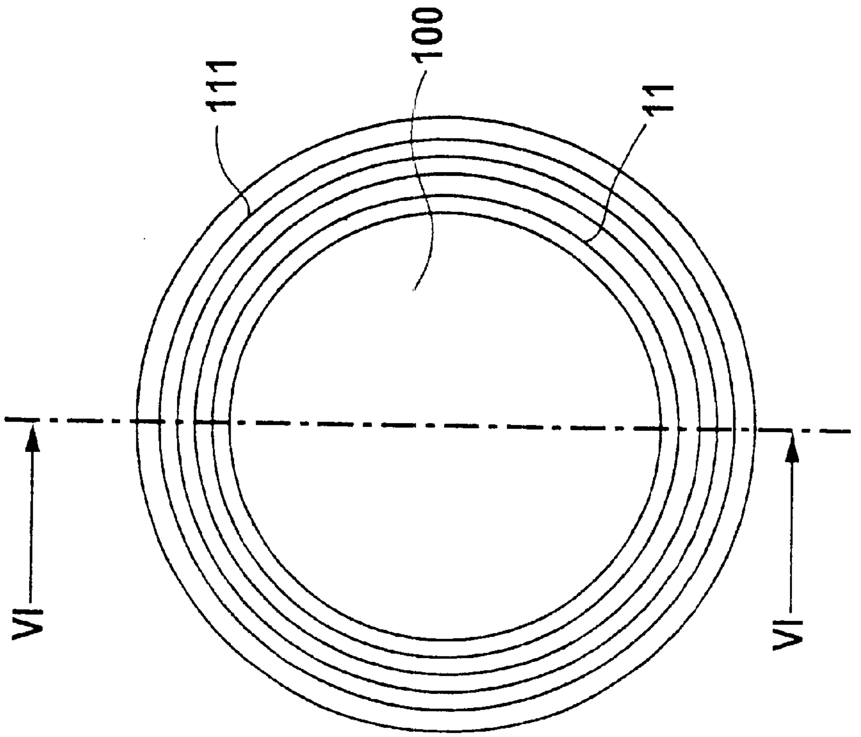

As is shown in FIG. 4 and FIG. 5, the desired effect is achieved by machining concentric rings 11 into one electrode surface 100. The concentric rings 11 have surfaces 111 which enclose a particular angle α with the originally flat electrode surface. As a result, the surfaces 111 of the rings slope relative to the axis of symmetry of the electrode. The rings 11 can each have a conical shape as seen in cross section, with the surfaces 111 forming lateral cone surfaces. Other geometries are also possible. The surfaces of the rings 11 could, for example, form curved surfaces of rotational solids. Spheroidal, ellipsoidal or paraboloidal surfaces are possible.

The angle α is calculated in such a way that the points of the normal cones through the respective centers of the rings all lie on the required focusing point. The following relation applies:

$$\sin\alpha=R_x/F$$

where $R_x$ is the central radius of the $x^{th}$ ring and F is the distance between the focus and the electrode surface. The width of the rings is advantageously chosen in such a way that the maximum heights of the rings over the central, i.e. flat electrode surface are <0.25*d, with d being the mean electrode spacing. This prevents the dielectric strength of the configuration from being lowered to an impermissible level. An additional requirement regarding the width of the rings is imposed by the permissible deviations in the position of the secondary foci relative to the common focus and the associated increase in the focus diameter.

An advantageous embodiment does not use the lateral surfaces of cones for the surfaces of the machined rings, as the simplest embodiment, but instead spherical surfaces having radii $r_x$ which are calculated in such a way that fine correction of the wave front in relation to the required focus position is accomplished:

$$r_x=F/\sin\alpha.$$

Further fine corrections of the type described permit the nonlinear effects caused by the division of the pressure wave into an intense shock wave to be corrected, allowing a focusing configuration with outstanding quality of focus to be produced with a quasi-planar configuration having a structured surface.

The properties of this configuration, which are described in detail, lead to self-focusing of the flat sound wave produced in the patent application cited above. This results in a self-focusing pressure-wave generator which is of extremely compact and simple construction and has a very long life. However, in very general terms, the surface structuring described above can also be used to focus or image in reflection any other flat or curved sound waves produced in some other way.

We claim:

1. An apparatus for producing shock waves for technical applications, comprising:

two electrodes;

a conductive liquid electrolyte disposed between said two electrodes; and a power pulse generator supplying an electric pulse to said electrodes for heating said conductive liquid electrolyte, thereby, producing acoustic sound waves without generating an electric arc.

2. The apparatus according to claim 1, wherein said conductive liquid electrolyte forms a liquid layer having large-area surfaces delimited by said two electrodes, said two electrodes inputting current, and at least one of said two electrodes allowing the sound waves that arise to be output.

3. The apparatus according to claim 1, wherein said conductive liquid electrolyte forms a liquid layer having narrow sides, said electrodes delimit said liquid layer at said narrow sides and input current, and an insulating membrane permits the sound waves that arise to be output.

4. The apparatus according to claim 1, wherein said two electrodes include a first, fixed, solid electrode and a second, thin, lightweight electrode at a given distance from said first electrode, said electrolyte having a specified layer thickness.

5. The apparatus according to claim 1, wherein said two electrodes include a first, fixed, solid electrode and a second electrode at a given distance from said first electrode, and said second electrode is a high-transmission grid.

6. The apparatus according to claim 1, wherein said electrodes are formed of corrosion-resistant materials.

7. The apparatus according to claim 1, wherein said two electrodes are first and second electrodes, said electrodes, said electrolyte and a sound propagation medium have a density and a sound velocity, and a product of the density and the sound velocity of said first electrode is significantly larger than products of the density and the sound velocity for said electrolyte and for the sound propagation medium.

8. The apparatus according to claim 1, wherein said electrolyte and a sound propagation medium have a density and a sound velocity, and a product of the density and the sound velocity of said electrolyte is approximately equal to a product of the density and the sound velocity of the sound propagation medium and of water.

9. The apparatus according to claim 1, wherein said electrodes are flat electrodes producing a flat sound wave front.

10. The apparatus according to claim 1, wherein said electrodes have an output side, and an acoustic lens is disposed on said output side of said electrodes.

11. The apparatus according to claim 1, wherein at least one of said electrodes is an acoustically hard electrode having a surface with structuring.

12. The apparatus according to claim 11, wherein said structuring includes concentric rings having surfaces enclosing a specified angle with said electrode surface.

13. The apparatus according to claim 12, wherein said rings each have a conical cross-sectional shape.

14. The apparatus according to claim 13, wherein said surfaces of said rings form lateral surfaces of cones.

15. The apparatus according to claim 13, wherein said surfaces of said rings form concavely curved surfaces of bodies of revolution.

16. The apparatus according to claim 15, wherein said surfaces of said bodies of revolution are selected from the group consisting of spheroidal surfaces, ellipsoidal surfaces and paraboloidal surfaces.

17. The apparatus according to claim 1, wherein at least one of said electrodes is concave for generating a curved wave front.

18. The apparatus according to claim 1, wherein said power pulse generator includes an LC element and an electronic switching element.

19. The apparatus according to claim 1, wherein said electrolyte has an electrical conductivity set for optimizing power matching to said power pulse generator.

20. The apparatus according to claim 1, including a degasser for said electrolyte.

21. The apparatus according to claim 1, including a fine filter for said electrolyte.

22. The apparatus according to claim 1, wherein said conductive liquid electrolyte has a value $(DV/V_o)/W$ being of the order of 0.015% to 0.07% per Joule per cubic centimeter, wherein $DV/V_o$ is a relative change in volume per W of energy input.

23. The apparatus according to claim 1, wherein said electrolyte is formed of simple alcohols with ion-conductive additives.

24. The apparatus according to claim 23, wherein said simple alcohols are selected from the group consisting of ethanol and methanol.

25. The apparatus according to claim 1, wherein said electrolyte is formed of polyhydric alcohols with ion-conductive additives.

26. The apparatus according to claim 25, wherein said polyhydric alcohols are selected from the group consisting of ethylene glycol and glycerol.

27. The apparatus according to claim 1, wherein said electrodes have a shape optimized to produce a nonpunctiform focus as required by a technical application.

28. The apparatus according to claim 1, wherein at least one of said electrodes is convex for producing a curved, diverging sound wave front.

29. The apparatus according to claim 1, wherein said conductive liquid electrolyte forms a liquid layer having large-area surfaces delimited by said two electrodes, said two electrodes inputting current, and at least one of said two electrodes allowing the sound waves that arise to be output.

30. An apparatus for producing shock waves for medical applications, such as for lithotripsy or pain therapy, comprising:

two electrodes;

a conductive liquid electrolyte disposed between said two electrodes; and a power pulse generator controlling said electrodes with an intense electric pulse for converting electrical energy directly into heat to heat said conductive liquid electrolyte and produce pressure pulsations output as acoustic sound waves into a sound propagation medium.

* * * * *